United States Patent
Sun

(10) Patent No.: US 9,241,823 B2
(45) Date of Patent: Jan. 26, 2016

(54) AUXILIARY DEVICE FOR MOUNTING NAIL DEFORMITY CORRECTION DEVICE AND NAIL DEFORMITY CORRECTION DEVICE MOUNTED ON A NAIL BY THE SAME

(71) Applicants: Dong Jun Sun, Seongnam-si (KR); GD Korea CO., LTD., Seongnam-si (KR)

(72) Inventor: Dong Jun Sun, Seongnam-si (KR)

(73) Assignees: Dong Jun Sun, Seongnam-Si, Gyeonggi-Do (KR); GD KOREA CO., LTD., Seongnam-Si, Gyeonggi-Do (KR)

( * ) Notice: Subject to any disclaimer, the term of this patent is extended or adjusted under 35 U.S.C. 154(b) by 360 days.

(21) Appl. No.: 13/851,780

(22) Filed: Mar. 27, 2013

(65) Prior Publication Data

US 2013/0267879 A1 Oct. 10, 2013

(30) Foreign Application Priority Data

Apr. 6, 2012 (KR) .......................... 10-2012-0036195

(51) Int. Cl.
*A61F 5/11* (2006.01)

(52) U.S. Cl.
CPC ........................................ *A61F 5/11* (2013.01)

(58) Field of Classification Search
CPC ....... A61F 5/11; A61F 5/019; A61F 5/05875; A61F 5/10
USPC .................. 602/22, 30, 31, 66; 128/893, 894; D24/107, 192, 231; 601/1
See application file for complete search history.

(56) References Cited

U.S. PATENT DOCUMENTS

| | | | | |
|---|---|---|---|---|
| 884,376 A | * | 4/1908 | Foster | 602/31 |
| 1,213,673 A | * | 1/1917 | Marvel | 602/31 |
| 1,420,085 A | * | 6/1922 | Figielek | 602/31 |
| 1,451,311 A | * | 4/1923 | Smith | 602/31 |
| 1,596,532 A | * | 8/1926 | Haener | 602/31 |
| 1,708,716 A | * | 4/1929 | Andersen | 602/31 |
| 2,024,412 A | * | 12/1935 | Wilson | 602/31 |
| 2,202,926 A | * | 6/1940 | Schmidthofer | 602/31 |
| 2,342,530 A | * | 2/1944 | Coates | 602/31 |
| 2,405,547 A | * | 8/1946 | Armagost | 602/31 |
| 2,499,851 A | * | 3/1950 | Cronholm | 602/31 |
| 2,505,086 A | * | 4/1950 | Andrews | 602/31 |
| 2,542,324 A | * | 2/1951 | Gibbons | 602/31 |
| 2,567,601 A | * | 9/1951 | Heinold et al. | 602/31 |
| 2,613,667 A | * | 10/1952 | Stanley | 602/31 |

(Continued)

FOREIGN PATENT DOCUMENTS

| | | |
|---|---|---|
| CA | 1100375 A1 | 5/1981 |
| CN | 1695571 A | 11/2005 |

(Continued)

*Primary Examiner* — Kim M Lewis
(74) *Attorney, Agent, or Firm* — Novick, Kim & Lee, PLLC; Jae Youn Kim

(57) ABSTRACT

There are provided an auxiliary device for mounting nail deformity correction device and a nail deformity correction device mounted on a nail by the same. The auxiliary device includes a resilient block that is placed in parallel with a finger and toe nail in a longitudinal direction of the finger and toe nail, and has elasticity to be elastically contracted and restored in a width direction of the finger and toe nail, and a pair of parallel protrusions that protrudes from an end of the resilient block to be inserted into an inside of the finger and toe nail, and is spaced apart from each other at a predetermined distance in the width direction of the finger and toe nail.

9 Claims, 4 Drawing Sheets

(56) References Cited

U.S. PATENT DOCUMENTS

| | | | | |
|---|---|---|---|---|
| 2,632,441 | A * | 3/1953 | Tuve | 602/31 |
| 5,261,872 | A * | 11/1993 | Goldenberg | 602/31 |
| 6,095,995 | A * | 8/2000 | Machida | 602/30 |
| 8,262,600 | B2 * | 9/2012 | Stolz | 602/31 |
| 8,435,200 | B2 * | 5/2013 | Yoshikawa | 602/31 |
| 2009/0204045 | A1 * | 8/2009 | Kim | 602/31 |
| 2010/0228173 | A1 * | 9/2010 | Ishida et al. | 602/31 |
| 2012/0310231 | A1 * | 12/2012 | McErlean et al. | 606/33 |
| 2013/0102942 | A1 * | 4/2013 | Tanaka et al. | 602/31 |

FOREIGN PATENT DOCUMENTS

| | | |
|---|---|---|
| JP | H11-348 A | 1/1999 |
| JP | 2003-010218 A | 1/2003 |
| KR | 10-2005-0072348 A1 | 5/2007 |
| KR | 10-2006-0094451 A1 | 9/2007 |
| WO | 2011/064889 A1 | 6/2011 |

* cited by examiner

AUXILIARY DEVICE FOR MOUNTING NAIL DEFORMITY CORRECTION DEVICE AND NAIL DEFORMITY CORRECTION DEVICE MOUNTED ON A NAIL BY THE SAME

CROSS-REFERENCE TO RELATED APPLICATIONS

This application claims the priority of Korean Patent Application No. 10-2012-0036195 filed on Apr. 6, 2012, in the Korean Intellectual Property Office, the disclosure of which is incorporated herein by reference.

BACKGROUND OF THE INVENTION

1. Field of the Invention

The present invention relates to an auxiliary device for mounting nail deformity correction device, and a nail deformity correction device mounted on a nail by the same, and more particularly, to an auxiliary device for mounting nail deformity correction device, and a nail deformity correction device mounted on a nail by the same, capable of easily mounting the nail deformity correction device on a deformed fingernail or toenail.

2. Description of the Related Art

A fingernail or a toenail is formed by the transformation of the skin, has certain hardness, and grows outward from an end of a finger or a toe. In a normal state, the fingernail or the toenail is gently bent in a rounded shape to be in close contact with a skin of the fingernail or toenail.

However, the fingernail or the toenail may be deformed in an abnormal shape by congenital or acquired factors. The deformed fingernail or toenail may give a bad impression in external appearance, and may involve health problems. In particular, an ingrown nail in which side ends of the fingernail or the toenail are curved in to dig into the skin causes intense pain to incapacitate a normal daily life. When the ingrown nail is continually neglected, the ingrown nail enters an inside of subcutaneous tissue to cause bleeding, and tissue necrosis of the finger or the toe occurs to provide a cause of a secondary inspection. The deformation of the fingernail or the toenail may be caused by the congenital factors, but may be caused by personal habits such as a gait in many cases. Further, the deformation of the fingernail may be caused by a disease such as an athlete's foot fungus that enters the fingernail or the toenail to deform a shape of the nail.

Conventionally, there has been used a correction device called a nail deformity correction device to correct such a deformed fingernail or toenail to a normal state. The nail deformity correction device is formed to be inserted into the deformed fingernail or toenail, and the inserted nail deformity correction device presses the side ends of the curved fingernail or toenail to straighten in a normal state. Examples of the correction device are disclosed in Korean Patent Nos. 10-0720646 and 10-0756079 in which a correction device is formed to be bent in a clip shape, or a correction device has both ends provided with hook portions and maintains elasticity using shape-memory alloy.

However, there is a disadvantage in that such a nail deformity correction device is difficult to be appropriately inserted into the deformed fingernail or toenail. That is, in order to mount the correction device on deformed fingernails or deformed toenails having different degrees from each other, the curved side ends are forcibly straightened using tweezers, and when unaccustomed to such a work, it may be difficult to insert the correction device into the nail, or the forcible insertion of the correction device may cause pain.

In addition, since the conventional nail deformity correction device has a shape, such as a clip shape, difficult to be in close contact with the fingernail or toenail or does not have a sufficient thin thickness, there is a disadvantage in that the conventional nail deformity correction device is not in close contact with the fingernail or the toenail. Accordingly, an unnecessary pressure is applied to the fingernail or the toenail, and since the wearer does not put on socks or shoes while the correction device is mounted thereon, there is a problem in his or her daily life. In addition, when the correction device maintains elasticity using shape-memory alloy affected by a body temperature, since excessive elasticity due to an unexpected temperature change is applied to the correction device, the fingernail or the toenail to be corrected may be pressed, or since the elasticity is rapidly decreased, a correction effect may not be exhibited.

CITATION LIST

Patent Document

Patent Document 1: Korean Patent No. 10-0720646 (May 21, 2007; see FIG. 1)
Patent Document 2: Korean Patent No. 10-0756079 (Sep. 11, 2007; see FIG. 3)

SUMMARY OF THE INVENTION

In view of the forgoing, an aspect of the present invention provides an auxiliary device for mounting nail deformity correction device capable of easily mounting a nail deformity correction device on a deformed fingernail or toenail, and a nail deformity correction device that is mounted on a nail by the same and maintains predetermined elasticity regardless of a body temperature.

It is to be understood that technical objects to be achieved by the present invention are not limited to the aforementioned objects and other technical objects which are not mentioned will be apparent from the following description to the person with an ordinary skill in the art to which the present invention pertains.

According to an aspect of the present invention, there is provided an auxiliary device for mounting nail deformity correction device including a square-shaped resilient block that is placed in parallel with a finger and toe nail to be corrected in a longitudinal direction of the finger and toe nail whose side ends are curved in to be deformed, and has elasticity to be elastically contracted and restored in a width direction of the finger and toe nail; and a pair of parallel protrusions that protrudes from an end of the resilient block to be inserted into an inside of the finger and toe nail, and is spaced apart from each other at a predetermined distance in the width direction of the finger and toe nail to be hooked into both side ends of the finger and toe nail. The protrusions that are in close contact with the both side ends in an opposite direction to each other due to a restoration force of the resilient block may straighten the finger and toe nail in the width direction.

The resilient block may be made of resilient resin.

The resilient block may include a supporting plate that maintains predetermined elasticity, and a first resilient resin layer that is layered on a surface of the supporting plate to reinforce the elasticity of the supporting plate.

The resilient block may have a plate shape, and may be bent upward or downward when the resilient block is contracted in the width direction of the finger and toe nail.

The auxiliary device for mounting nail deformity correction device may further include a guide groove that is formed by indenting a part of the resilient block between the protrusions in the longitudinal direction of the finger and toe nail, and the resilient block may be symmetrically contracted and restored about the guide groove.

The guide groove may include an opening portion that is opened between the protrusions and has a predetermined width, and an indented portion that has a width gradually reduced toward an inside of the resilient block and forms a sharp panel point on an end thereof.

According to another aspect of the present invention, there is provided a nail deformity correction device that is slidably combined with the auxiliary device for mounting nail deformity correction device of the present invention. The nail deformity correction device includes a resilient bar that extends in a width direction of a finger and toe nail to be corrected, has predetermined elasticity to be bent and to be elastically restored regardless of a body temperature, and is in close contact with an upper surface of the resilient block; and a pair of hook portions that is bent downward from both ends of the resilient bar, and is provided with accommodation grooves for accommodating an end of the resilient block between the resilient bar and the hook portions. The resilient bar may be moved to the finger and toe nail to be in close contact with the upper surface of the finger and toe nail, and the hook portions may be mounted to be hooked into both side ends of the finger and toe nail.

The resilient bar may include a supporting member that is formed to extend in the width direction of the finger and toe nail and maintains predetermined elasticity, and a second resilient resin layer that is layered on a surface of the supporting member to reinforce the supporting member.

The nail deformity correction device may be packaged with the auxiliary device for mounting nail deformity correction device, and the nail deformity correction device may include a plurality of nail deformity correction devices having different lengths from each other.

BRIEF DESCRIPTION OF THE DRAWINGS

The above and other aspects, features and other advantages of the present invention will be more clearly understood from the following detailed description taken in conjunction with the accompanying drawings, in which.

DETAILED DESCRIPTION OF THE PREFERRED EMBODIMENT

Figure 1:
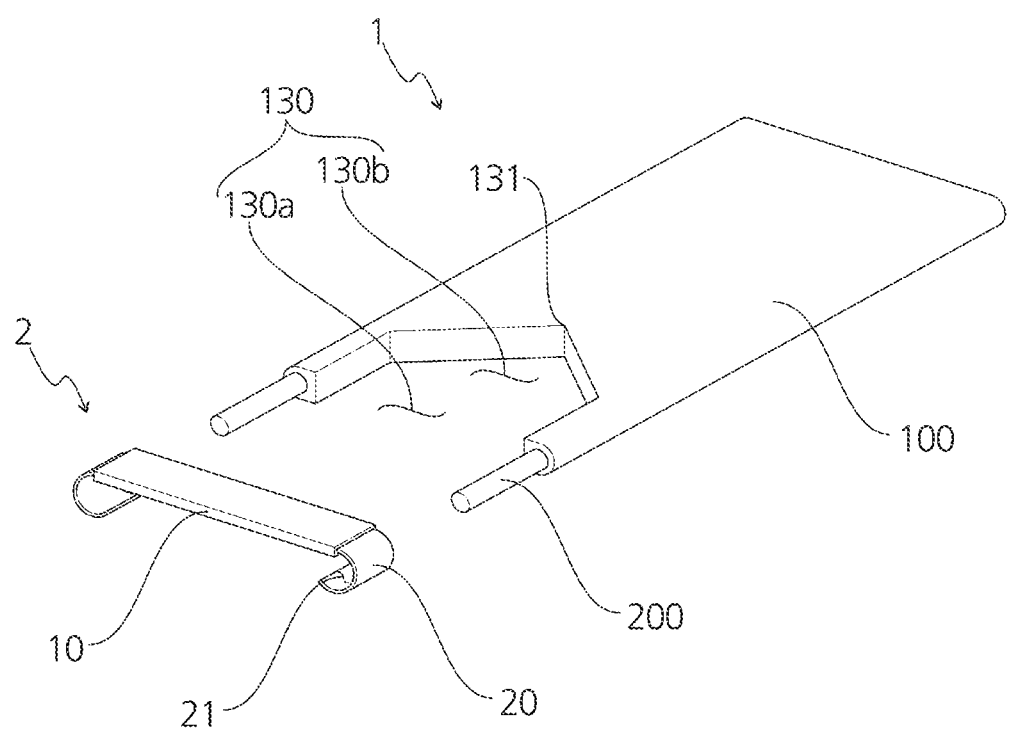
FIG. 1 is a perspective view of an auxiliary device for mounting nail deformity correction device, and a nail deformity correction device mounted on a nail by the same according to an embodiment of the present invention.

Exemplary embodiments of the present invention will now be described in detail with reference to the accompanying drawings.

As set forth above, according to exemplary embodiments of the invention, since an auxiliary device for mounting nail deformity correction device is elastically contracted or expanded, a deformed fingernail or toenail is straightened to have an appropriate width, so that it is possible to easily mounting the nail deformity correction device.

Further, according to exemplary embodiments of the invention, a nail deformity correction device can be completely in close contact with a fingernail or a toenail to be corrected. Since the nail deformity correction device has predetermined elasticity, a correction effect of a deformed fingernail or toenail can be maximized. In addition, a wearer wearing the correction device can normally live in his or her daily life.

While the present invention has been explained and described in connection with the exemplary embodiments, it will be apparent to those skilled in the art that modifications and variations can be made without departing from the spirit and scope of the invention as defined by the appended claims.

Merits and features of the present invention, and methods for accomplishing them will become more apparent from the following embodiments taken in conjunction with the accompanying drawings. However, the present invention is not limited to the disclosed embodiments, but may be implemented in various manners. The embodiments are provided to complete the disclosure of the present invention and to allow those having ordinary skill in the art to understand the scope of the present invention. The present invention is defined by the category of the claims. Through the present specification, parts having substantially same configuration will be assigned same reference numerals.

Hereinafter, an auxiliary device for mounting nail deformity correction device, and a nail deformity correction device mounted on a nail by the same according to an embodiment of the present invention will be described in detail with reference to FIGS. 1 to 6.

Figure 2:
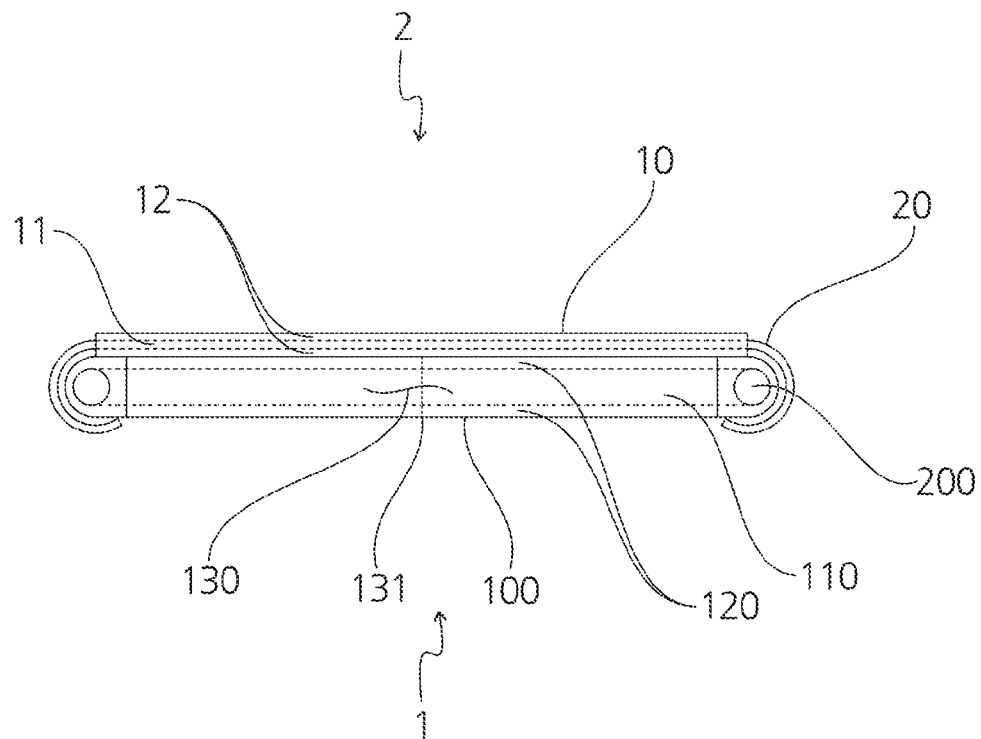
FIG. 2 is a front view illustrating a state where the auxiliary device for mounting nail deformity correction device and the nail deformity correction device illustrated in FIG. 1 are combined with each other.

FIG. 1 is a perspective view of an auxiliary device for mounting nail deformity correction device, and a nail deformity correction device mounted on a nail by the same according to an embodiment of the present invention, and FIG. 2 is a front view illustrating a state where the auxiliary device for mounting nail deformity correction device and the nail deformity correction device illustrated in FIG. 1 are combined with each other.

As illustrated in FIG. 1, an auxiliary device 1 for mounting a nail deformity correction device 2 according to an embodiment of the present invention mainly includes a resilient block 100 having a square shape and protrusions 200 for insertion into a finger or a toe nail to be corrected. The nail deformity correction device 2 that is elastically mounted on the finger or the toe nail to be corrected mainly includes a resilient bar 10 and hook portions 20.

In the present specification, a "nail" or a "finger and toe nail" may refer to a fingernail or a toenail that grows outward from an end of a finger or a toe. The "nail" or the "finger and toe nail" may mean a part of the body which the nail deformity correction device 2 of the present invention is mounted on or the protrusions 200 are inserted into, and, for example, the mounting on or inserting into the finger and toe nail may mean that the nail deformity correction device is mounted on or inserted into any one of the fingernail or the toenail. To provide a more concise description, the fingernail or the toenail may be referred to as the 'finger and toe nail' in the present specification. Further, in the present specification, a 'longitudinal direction' of the finger and toe nail may generally mean a direction in which the finger and toe nail grows, and a 'width direction' of the finger and toe nail may mean a direction perpendicular to the longitudinal direction, that is, a direction in which the finger and toe nail to be corrected is deformed to be curved.

The auxiliary device for mounting nail deformity correction device 1 is placed in parallel with the finger and toe nail in a longitudinal direction of the finger and toe nail by inserting the protrusions 200 into the inside of the finger and toe nail to be corrected. The nail deformity correction 2 is slidably combined with the resilient block 100 of the auxiliary device for mounting nail deformity correction device 1 using the hook portions 20 formed at ends thereof. Thus, the nail deformity correction device 2 can be moved along the resilient block 100 in parallel, pass through the protrusions 200, and then be mounted on the finger and toe nail to be corrected into which the protrusions 200 have been inserted. At this time, the auxiliary device for mounting nail deformity correction device 1 can appropriately straighten the finger and toe nail to be corrected in which side ends, preferably, both side ends are curved in to be deformed, using elasticity of the resilient block 100. In this way, the nail deformity correction device 2 can easily be moved on the finger and toe nail to be corrected and mounted thereon. A process of mounting the nail deformity correction device 2 will be described below in more detail, and components of the auxiliary device for mounting nail deformity correction device 1 and the nail deformity correction device 2 will be described in more detail with reference to FIGS. 1 and 2.

The resilient block 100 functions as a body of the auxiliary device for mounting nail deformity correction device 1, and is formed as a square-shaped block as a whole. As described above, the resilient block 100 is placed in the longitudinal direction of the finger and toe nail such that one end thereof provided with the protrusions 200 faces the finger and toe nail to be corrected. The resilient block 100 has a rectangular shape whose one side extends long as illustrated in the figure, but is not limited thereto. The shape of the resilient block may be changed depending on a width of the finger and toe nail to be corrected or the entire size thereof. Further, a width, a thickness, or a length thereof may also be appropriately adjusted. Preferably, the resilient block 100 may be formed as a square-shaped block as a whole, and may be formed as a flat plate type block having a relatively thin thickness. The thickness of the resilient block 100 may be set, but not limited thereto, to be 1.5 mm to 2.5 mm, preferably, 2 mm. Thus, it is possible to mount the nail deformity correction device 2 on the nail.

The resilient block 100 has elasticity, and, thus, is elastically contracted or is reversely expanded to be restored in a width direction of the finger and toe nail. To this achieve, the resilient block 100 may be made of a resilient material. The resilient block may be made of at least one metal selected from among aluminum, stainless steel and titanium, or may be made of at least one resilient resin selected from among polyamide, polyester, polycarbonate, polyethylene, acrylonitrile-butadiene-styrene copolymer resin (ABS), polystyrene and cellulose.

Further, the resilient block 100 includes a supporting plate 110 that maintains certain elasticity, and a first resilient resin layer 120 that is layered on a surface of the supporting plate 110 to reinforce elasticity of the supporting plate 110. The supporting plate 110 may be made of at least one selected from among aluminum, stainless steel, and titanium. The first resilient resin layer 120 may be made of at least one resilient resin selected from among polyamide, polyester, polycarbonate, polyethylene, acrylonitrile-butadiene-styrene copolymer resin (ABS), polystyrene and cellulose.

The resilient block 100 may have, but not limited thereto, yield strength of 5 MPa to 20 MPa, and Vickers hardness of 200 HV to 480 HV. Within the above-described range of the yield strength and the hardness, it is possible to easily manipulate the auxiliary device and to appropriately straighten the finger and toe nail to be corrected.

In particular, by using the resilient block 100 formed as a flat plate type block, when contracted in the width direction of the finger and toe nail, the resilient block can be bent upward or downward, so that it is possible to easily change its shape. Here, the upward means a direction in which the skin of finger and toes faces the finger and toe nail, and the downward means a direction opposite to the upward.

Meanwhile, a guide groove 130 formed by indenting a part of the resilient block 100 is formed in the resilient block 100. The guide groove 130 may be formed toward the inside of the resilient block 100 to be indented in the longitudinal direction of the finger and toe nail between the protrusions 200, and the resilient block 100 may have a symmetrical shape about the guide groove 130. Thus, when an external force is applied to left and right sides of the resilient block 100, the resilient block 100 is symmetrically contracted about the guide groove 130, and when the external force is removed, the resilient block is immediately restored to be symmetric.

As illustrated in the figure, such a guide groove 130 has an opening portion 130a formed to be opened between the protrusions 200 so as to have a certain width, and an indented portion 130b that has a width gradually reduced toward the inside of the resilient block 100 and forms a sharp panel point 131 on an end portion thereof. In such a case, a portion around the panel point 131 becomes a free end to be easily deformed, and the panel point 131 allows the resilient block 100 to be deformed so as to be easily contracted or expanded again.

The protrusions 200 are paired with each other, and protrude from one end of the resilient block 100 to be inserted into the inside of the finger and toe nail to be corrected. The protrusions 200 protrude from the resilient block 100 in parallel with each other, and are spaced apart from at a certain distance in the width direction of the finger and toe nail to be hooked into the both side ends of the curved finger and toe nail to be corrected. The protrusions 200 are elastically close to each other or separated from each other by the contraction or the restoration of the resilient block 100. Accordingly, the contracted protrusions 200 by applying the external force to the sides of the resilient block 100 are inserted, and then the external force is removed, so that a distance between the protrusions 200 increases. Thus, the respective protrusions 200 are in close contact with the both side ends of the finger and toe nail to be corrected in an opposite direction to each other. As a result, the both side ends are continuously pressed by a restoration force of the resilient block 100, so that it is possible to appropriately straighten the curved finger and toe nail.

The protrusions 200 may be made of the same material as that of the resilient block 100 to be integrally formed with the resilient block, or may be made of a different material from that of the resilient block. The protrusions 200 may be made of a material of high hardness, such as a metal material, and may have certain elasticity. In addition, although not illustrated, the protrusions 200 may be formed such that the protrusions are connected to each other within the resilient block 100 to be elastically supported by each other. In particular, when the resilient block 100 includes the supporting plate 110, the protrusions 200 are integrally formed with the supporting plate 110.

The protrusions 200 may have a length of 2 mm to 5 mm and a thickness of 0.2 mm to 1 mm, and the length and thickness of the protrusions may be selected within the above-described range depending on the material of the protrusion. By way of example, when made of a steel plate, the protrusions may have a thickness of 0.2 mm, and when made of ordinary steel, the protrusions may have a thickness of 1 mm.

A resilient bar 10 of the nail deformity correction device 2 extends in the width direction of the finger and toe nail to be corrected. The resilient bar is bent due to the elasticity, and then is elastically restored again. When the nail deformity correction device 2 is combined with the auxiliary device for mounting nail deformity correction device 1, the resilient bar 10 is in close contact with an upper surface of the resilient block 100.

The resilient bar 10 may be made of a material having a thin thickness and high elasticity, and may be preferably made of a material that maintains certain elasticity regardless of a body temperature other than a material (for example, shape-memory alloy) whose shape changes depending on a body temperature. The body temperature means a temperature measured from a human body. For example, the body temperature may be about 25 degrees Celsius to about 40 degrees Celsius. The body temperature may be changed depending on a part of the body, and, for example, a foot temperature may be about 25 degrees Celsius to about 30 degrees Celsius.

For example, the resilient bar 10 may be made of at least one resilient resin selected from among polyamide, polyester, polycarbonate, polyethylene, acrylonitrile-butadiene-styrene copolymer resin (ABS), polystyrene and cellulose. Such a resilient bar made of resilient resin can maintain certain elasticity without being affected by the body temperature.

Further, the resilient bar 10 is formed to extend in the width direction of the finger and toe nail as illustrated in the figure, and includes a supporting member 11 for maintaining certain elasticity, and a second resilient resin layer 12 layered on a surface of the supporting member 11 to reinforce the elasticity of the supporting member 11. Accordingly, even when a temperature unexpectedly changes, the nail deformity correction device 2 can maintain appropriate elasticity using the resilient bar 10, so that an effect of correcting the finger and toe nail can be maximized. Preferably, the supporting member 11 may be made of at least one metal selected from among aluminum, stainless steel, and titanium. The second resilient resin layer 12 may be made of at least one resilient resin selected from among polyamide, polyester, polycarbonate, polyethylene, acrylonitrile-butadiene-styrene copolymer resin (ABS), polystyrene and cellulose. In addition, the second resilient resin layer 12 is interposed between the supporting member 11 and the finger and toe nail to be smoothly in close contact with a surface of the finger and toe nail. When made of metal, the supporting member 11 may have a thickness of about 0.25 mm to about 0.6 mm.

For example, the resilient bar 10 may have, but not limited thereto, yield strength of about 5 MPa to about 20 MPa, and Vickers hardness of about 200 HV to about 480 HV. Within the above-described range of the yield strength and the hardness, it is possible to easily manipulate the auxiliary device and to appropriately straighten the finger and toe nail to be corrected.

A length and a thickness of the resilient bar 10 may be changed depending on a curved degree of the finger and toe nail to be corrected and the entire size thereof. According to the embodiment of the present invention, the resilient bar 10 may preferably have a length equal to or slightly smaller than a distance between the both side ends of the finger and toe nail. The resilient bar 10 may have a thickness of 0.25 mm to 1 mm, and, preferably, 0.7 mm to 1 mm. Due to the resilient bar 10 having such a thin thickness, the nail deformity correction device 2 can be mounted on the surface of the finger and toe nail to be corrected so as to be completely in close contact with the surface of the finger and toe nail. Thus, since the wearer does not feel unnecessary pressure on an affected area around the deformed finger and toe nail, the wearer can put on, for example, socks or shoes while the nail deformity correction device 2 is mounted thereon, so that there is no problem in his or her daily life. As a result, the nail deformity correction device exhibits an advantage in that a period of mounting the nail deformity correction device 2 can extend as much as an effect of correcting the deformed nail can sufficiently exhibit.

The hook portions 20 are respectively bent downward in a hook-like shape from both ends of the resilient bar 10. Thus, accommodation grooves 21 for accommodating the end of the resilient block 100 are formed between the hook portions 20 and the resilient bar 10. The accommodation grooves 21 may have a width equal to or greater than the thickness of the resilient block 100. The accommodation grooves 21 may have, for example, a width of 1.5 mm to 2.5 mm so as to correspond to the thickness of the resilient block 100, and, preferably, 2 mm.

The hook portions 20 may be made of the same material as the resilient bar 10 to be integrally formed with the resilient bar, or may be made of a different material from the resilient bar. Similarly to the protrusions 200, the hook portions may be preferably made of a material of high hardness, for example, a metal material, and the hook portions may be integrally formed with the supporting member 11 by extending ends of the supporting member 11. In addition, portions of the hook portions 20 in close contact with the inside of the toe nail may have a length of 1.5 mm to 2.5 mm, and, preferably, 2 mm. Within such a range, it is possible to mount the nail deformity correction device on the toe nail, and to easily use the nail deformity correction device.

The nail deformity correction device 2 may be slidably combined with the resilient block 100 while the end of the resilient block 100 is accommodated in the accommodation grooves 21 and the resilient bar 10 is in close contact with the upper surface of the resilient block 100. In such a state, the nail deformity correction device 2 can be moved in parallel along the resilient block 100, and easily mounted on the finger and toe nail to be corrected while the resilient bar 10 of the nail deformity correction device 2 is elastically in close contact with an upper surface of the finger and toe nail and the hook portions 20 are hooked in the both curbed side ends of the finger and toe nail.

Hereinafter, a process of mounting the nail deformity correction device and a correction effect of the nail deformity correction device mounted on the finger and toe nail to be corrected will be described in more detail with reference to FIGS. 3 to 6.

Figure 3:
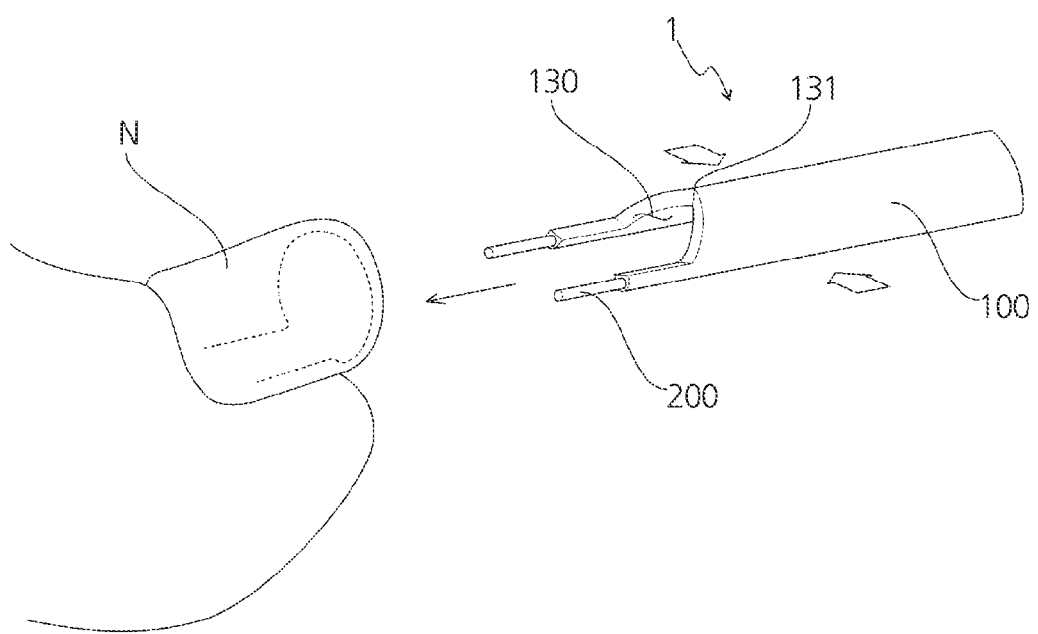
FIGS. 3 to 5 are diagrams illustrating a process of mounting the nail deformity correction device illustrated in FIG. 1 using the auxiliary device for mounting nail deformity correction device.
Figure 4:
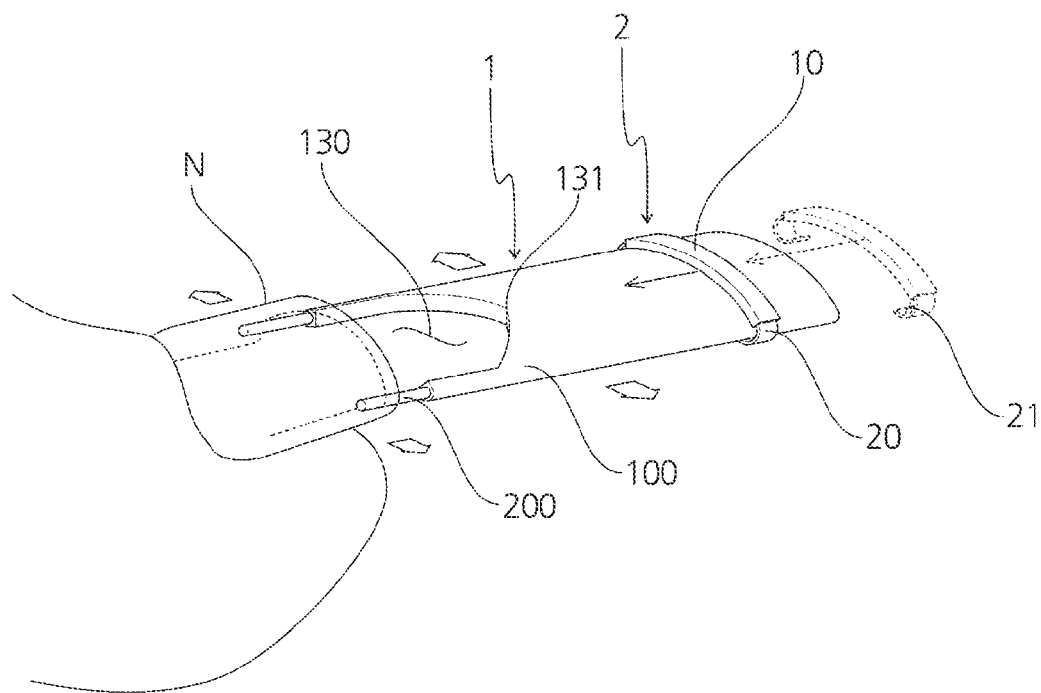
Figure 5:
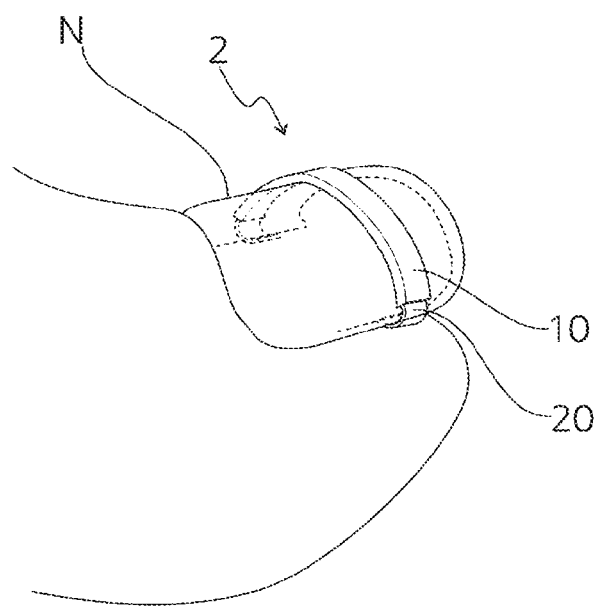
Figure 6:
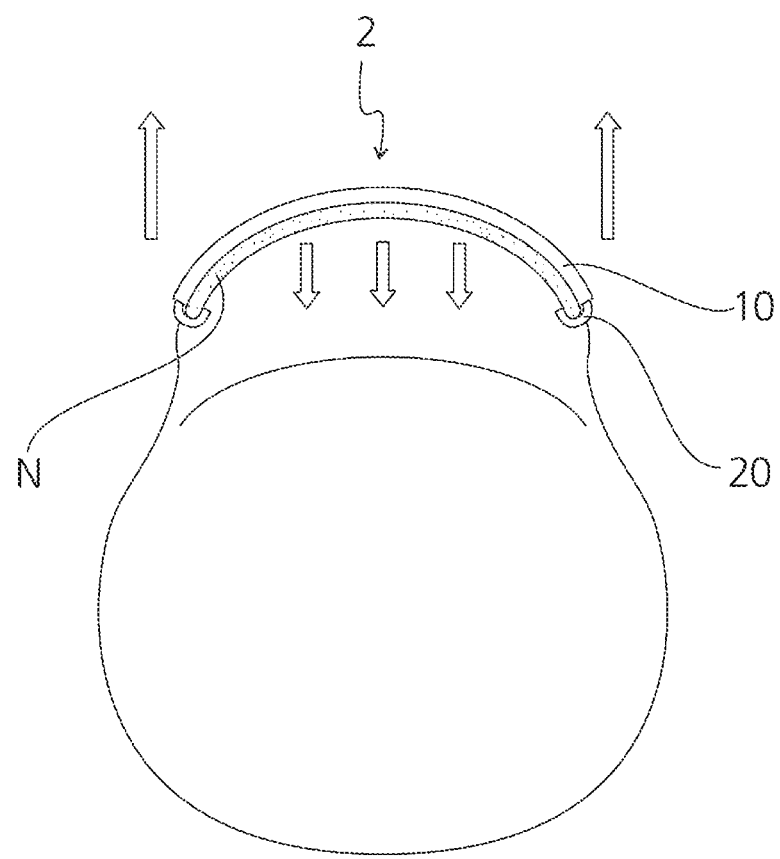
FIG. 6 is a conceptual diagram for describing a correction operation of the nail deformity correction device illustrated in FIG. 5.

FIGS. 3 to 5 are diagrams illustrating a process of mounting the nail deformity correction device illustrated in FIG. 1 using the auxiliary device for mounting nail deformity correction device, and FIG. 6 is a conceptual diagram for describing a correction operation of the nail deformity correction device illustrated in FIG. 5.

Referring to FIG. 3, a shape of a finger and toe nail N to be corrected is a rounded-bent shape as a whole in which both side ends are curved in the finger and toe nail N to be deformed as illustrated in the figure. In such a case, since a central portion of the finger and toe nail N expands upward, the central portion thereof is not in close contact with skins of fingers or toes, and the both curved side ends presses a skin tissue around the finger and toe nail N downward to thereby causing intense pain.

The auxiliary device for mounting nail deformity correction device 1 is placed in parallel with the finger and toe nail in the longitudinal direction of the finger and toe nail N, and the protrusions 200 are inserted into the inside of the ends of the finger and toe nail N. At this time, when an external force is applied to the both sides of the resilient block 100 in a direction indicated by arrow, the resilient block 100 is contracted, so that the distance between the protrusions 200 appropriately decreases. Thus, the protrusions 200 can be easily inserted into the inside of the finger and toe nail N. Since a width of the finger and toe nail N depends on the deformed degree of the finger and toe nail, the strength of the external force is adjusted, so that the distance between the protrusions 200 can also be appropriately adjusted.

In such an inserting process, the resilient block 100 is symmetrically contracted in the width direction of the finger and toe nail N about the guide groove 130, and in particular, the panel point 131 formed at the end of the guide groove 130 causes the deformation of a portion around the panel point. Accordingly, the resilient block 100 can be symmetrically contracted with ease as illustrated in the figure.

Subsequently, referring to FIG. 4, after the protrusions 200 are respectively inserted into the inside of the finger and toe nail N, when the external force is removed, the resilient block 100 can elastically expand due to the restoration force, so that the protrusions 200 are in close contact with the inside of the both side ends of the finger and toe nail N. In such a state, the auxiliary device for mounting nail deformity correction device 1 can appropriately straighten the deformed finger and toe nail N. At this time, the resilient block 100 can maintain elasticity in a slightly curved state, so that the finger and toe nail N can also be maintained in a straightened state.

In such a state, the nail deformity correction device 2 is slidably combined with the resilient block 100. That is, as illustrated in the figure, the nail deformity correction device 2 is combined through the end of the resilient block 100 in a direction parallel to the width direction of the finger and toe nail N, and the combined nail deformity correction device can be freely moved in the longitudinal direction of the finger and toe nail N along the resilient block 100. Thus, the nail deformity correction device 2 easily passes through the protrusions 200 to be easily mounted on the straightened finger and toe nail N. The nail deformity correction device 2 combined with the resilient block 100 is maintained in a slightly curved state similarly to the resilient block 100 so as to easily slide along the resilient block 100, and when the nail deformity correction device 2 is mounted on the finger and toe nail N, by separating the protrusions 200 from the finger and toe nail N, the auxiliary device for mounting nail deformity correction device 1 can be removed.

Referring to FIG. 5, the nail deformity correction device 2 is maintained in a state in close contact with the deformed finger and toe nail N. At this time, the second resilient resin layer (see reference numeral 12 of FIG. 2) formed on the surface of the nail deformity correction device 2 is interposed between the supporting member (see reference numeral 11 of FIG. 2) and the finger and toe nail N to be smoothly in close contact with the surface of the finger and toe nail N. That is, the second resilient resin layer 12 increases the elasticity of the resilient bar 10, and decreases friction between the nail deformity correction device 2 and the finger and toe nail N, so that the nail deformity correction device 2 can be smoothly mounted on the finger and toe nail without pain. Accordingly, the second resilient resin layer can help the nail deformity correction device 2 to be readily in close contact with the finger and toe nail N.

Referring to FIG. 6, the mounted nail deformity correction device 2 continuously presses the deformed finger and toe nail N upward and downward in a direction indicated by arrow, so that the deformed finger and toe nail N can be straightened to be a normal state. At this time, the resilient bar 10 presses the central portion of the finger and toe nail N downward while the resilient bar is in close contact with the upper surface of the finger and toe nail N, and the hook portions 20 press the both side ends of the finger and toe nail N upward. Accordingly, the expanded central portion due to the deformation is straightened downward, and the both curved side ends are straightened outward, so that the deformed finger and toe nail can be corrected to be a normal state.

Meanwhile, for the sake of the convenience, the nail deformity correction device 2 may be packaged with the auxiliary device for mounting nail deformity correction device (see reference numeral 1 of FIG. 1). At this time, the nail deformity correction device 2 and the auxiliary device for mounting nail deformity correction device 1 may be individually packaged, and then repackaged in one package, or may be packaged together in one package.

When packaged together, a plurality of nail deformity correction devices 2 having different lengths may be provided as one set so as to appropriately correct the finger and toe nails N having different widths depending on the deformed degree. For example, each of the nail deformity correction devices 2 may have lengths of 16.5 mm, 18 mm, 19.5 mm, 21 mm, 22.5 mm, 24 mm, or 28 mm. At this time, the resilient bars 10 of the respective nail deformity correction devices 2 included in the set may also have different lengths from each other so as to correspond to the widths of the finger and toe nails N. In addition, the set of the nail deformity correction devices 2 may be provide together with an auxiliary device set including the auxiliary device for mounting nail deformity correction device 1 to be configured as a nail deformity correction kit. Thus, when the nail deformity correction devices 2 having different lengths from each other are used together with the auxiliary device of mounting nail deformity correction device 1 provided in the nail deformity correction kit, the finger and toe nails N deformed in different sizes from each other can be further appropriately corrected.

Moreover, according to a specific example of the nail deformity correction device 2, a metal plate made of a stainless steel (SUS304) material is cut to have a thickness of 0.1 mm to 0.6 mm, a length of 16 mm to 36 mm, and a width of 10 mm to 30 mm using a press, and is then cleaned using ultrasonic waves. The cleaned metal plate is electropolished, and is then cleaned using ultrasonic waves again. In this way, the supporting member (reference numeral 11 of the FIG. 2) is prepared. Thereafter, the supporting member 11 is provided into a mold for coating with resin, and a thermoplastic polyamide resin composition (Grilamid TR90, EMS-DHEMIE (Korea) Ltd., Korea) is input. The second resilient resin layer (reference numeral 12 of FIG. 2) is formed using a cylinder compression method under a condition of about 270 degrees Celsius. Subsequently, both ends of the exposed supporting member are cut in a U shape by a press to produce the nail deformity correction device 2 having the shape illustrated in FIG. 1. The produced nail deformity correction device 2 is sterilized with Ethylene Oxide (EO) gas and is then packaged.

In addition, according to a specific example of the auxiliary device for mounting nail deformity correction device 1, a metal plate made of a stainless steel material is cut to have a thickness of 0.2 mm to 1 mm using a press, and is then cleaned using ultrasonic waves. The cleaned metal plate is electropolished, and is then cleaned using ultrasonic waves again. In this way, the supporting plate (reference numeral 110 of the FIG. 2) for forming the protrusions is prepared. Thereafter, the supporting plate 110 is provided into a mold for coating with resin, and a thermoplastic polyamide resin composition (Grilamid TR90, EMS-DHEMIE (Korea) Ltd., Korea) is input. The first resilient resin layer (reference numeral 120 of FIG. 2) is formed using a cylinder compression method under a condition of about 270 degrees Celsius. At this time, the protrusions 20 may have a length of 2 mm to 5 mm and a thickness of 0.2 mm to 1 mm. In this way, the auxiliary device for mounting nail deformity correction device 1 having the shape illustrated FIG. 1 can be produced. The produced auxiliary device for mounting nail deformity correction device 1 is sterilized with Ethylene Oxide (EO) gas and is then packaged.

Although the present invention has been described in conjunction with the accompanying drawings and the exemplary embodiments, it should be understood by those skilled in the art that the present invention can be implemented in other specific forms without changing the technical spirit and essential features of the present invention. Accordingly, the above-described exemplary embodiments are merely illustrative examples in all aspects but not limited to the exemplary embodiments.

EXPLANATION OF REFERENCE NUMERALS

1: Auxiliary device for mounting nail deformity correction device
2: Nail deformity correction device
10: Resilient bar
11: Supporting member
12: Second resilient resin layer
20: Hook portion
21: Accommodation groove
100: Resilient block
110: Supporting plate
120: First resilient resin layer
130: Guide groove
130a: Opening portion
130b: Indented portion
131: Panel point
200: Protrusion
N: Finger and toe nail

What is claimed is:

1. An auxiliary device for mounting a nail deformity correction device, the auxiliary device comprising:
a resilient block that is configured to be placed in parallel with a finger or a toe nail to be corrected in a longitudinal direction of the finger or the toe nail whose both side ends are curved in to be deformed, and has elasticity to be elastically contracted and restored in a width direction of the finger or the toe nail;
a pair of parallel protrusions that protrudes from an end of the resilient block for insertion into an inside of the finger or the toe nail, and is spaced apart from each other at a predetermined distance in the width direction of the finger or the toe nail to be hooked into the both side ends of the finger or the toe nail; and
a guide groove that is formed by indenting a part of the resilient block between the protrusions in the longitudinal direction of the finger or the toe nail,
wherein the protrusions that are in close contact with the both side ends in an opposite direction to each other due to a restoration force of the resilient block straighten the finger or the toe nail in the width direction, and
wherein the resilient block is symmetrically contracted and restored about the guide groove.

2. The auxiliary device for mounting the nail deformity correction device according to claim 1, wherein the resilient block is made of resilient resin.

3. The auxiliary device for mounting the nail deformity correction device according to claim 1, wherein the resilient block includes a supporting plate that maintains predetermined elasticity, and a first resilient resin layer that is layered on a surface of the supporting plate to reinforce the elasticity of the supporting plate.

4. The auxiliary device for mounting the nail deformity correction device according to claim 1, wherein the resilient block has a plate shape, and is bent upward or downward when the resilient block is contracted in the width direction of the finger or the toe nail.

5. The auxiliary device for mounting the nail deformity correction device according to claim 1, wherein the guide groove includes an opening portion that is opened between the protrusions and has a predetermined width, and an indented portion that has a width gradually reduced toward an inside of the resilient block and forms a sharp panel point on an end thereof.

6. An auxiliary device for mounting a nail deformity correction device, the auxiliary device comprising:
a resilient block that is configured to be placed in parallel with a finger or a toe nail to be corrected in a longitudinal direction of the finger or the toe nail whose both side ends are curved in to be deformed, and has elasticity to be elastically contracted and restored in a width direction of the finger or the toe nail; and
a pair of parallel protrusions that protrudes from an end of the resilient block for insertion into an inside of the finger or the toe nail, and is spaced apart from each other at a predetermined distance in the width direction of the finger or the toe nail to be hooked into the both side ends of the finger or the toe nail,
wherein the protrusions that are in close contact with the both side ends in an opposite direction to each other due to a restoration force of the resilient block straighten the finger or the toe nail in the width direction,
wherein the nail deformity correction device is configured to be slidably combined with the auxiliary device,
wherein the nail deformity correction device comprises:
a resilient bar that extends in the width direction of the finger or the toe nail to be corrected, has predetermined elasticity to be bent and to be elastically restored regardless of a body temperature, and is configured to be in close contact with an upper surface of the resilient block; and
a pair of hook portions that is bent downward from both ends of the resilient bar, and is provided with accommodation grooves for accommodating an end of the resilient block between the resilient bar and the hook portions, and
wherein the resilient bar is configured to be moved to the finger or the toe nail and configured to be in close contact with the upper surface of the finger or the toe nail, and the hook portions are configured to be mounted and hooked into the both side ends of the finger or the toe nail.

7. The auxiliary device for mounting the nail deformity correction device according to claim 6, wherein the resilient bar includes a supporting member that is formed to extend in the width direction of the finger or the toe nail and maintains predetermined elasticity, and a second resilient resin layer that is layered on a surface of the supporting member to reinforce the supporting member.

8. The auxiliary device for mounting the nail deformity correction device according to claim 6, wherein the nail deformity correction device is packaged with the auxiliary device for mounting the nail deformity correction device.

9. The auxiliary device for mounting the nail deformity correction device according to claim 8, wherein the nail deformity correction device is one of a plurality of nail deformity correction devices having different lengths from each other.

* * * * *